US012594338B2

(12) United States Patent
Aboussekhra et al.

(10) Patent No.: US 12,594,338 B2
(45) Date of Patent: *Apr. 7, 2026

(54) CISPLATIN ANALOGUE WITH POTENT ANTI-CANCER EFFECTS AND SYNTHESIS THEREOF

(71) Applicant: King Faisal Specialist Hospital & Research Centre, Riyadh (SA)

(72) Inventors: Abdelilah Aboussekhra, Riyadh (SA); Ibrahim Al-Jammaz, Riyadh (SA); Basem Al-Otaibi, Riyadh (SA); Noura N. Alraouji, Riyadh (SA)

(73) Assignee: King Faisal Specialist Hospital & Research Centre, Riyadh (SA)

( * ) Notice: Subject to any disclaimer, the term of this patent is extended or adjusted under 35 U.S.C. 154(b) by 230 days.

This patent is subject to a terminal disclaimer.

(21) Appl. No.: 18/227,094

(22) Filed: Jul. 27, 2023

(65) Prior Publication Data

US 2024/0042040 A1 Feb. 8, 2024

Related U.S. Application Data

(62) Division of application No. 17/877,339, filed on Jul. 29, 2022, now Pat. No. 12,186,399.

(51) Int. Cl.

| | |
|---|---|
| ***A61K 47/54*** | (2017.01) |
| ***A61K 45/06*** | (2006.01) |
| ***A61P 35/00*** | (2006.01) |

(52) U.S. Cl.
CPC .............. *A61K 47/54* (2017.08); *A61K 45/06* (2013.01); *A61P 35/00* (2018.01)

(58) Field of Classification Search
CPC ....... C07F 15/0093; A61P 35/00; A61K 47/54
See application file for complete search history.

(56) References Cited

PUBLICATIONS

Fathy et al., Molecules, vol. 24, pp. 1-14, publ. Nov. 3, 2019 (Year: 2019).*
Bohme, David & Beck-Sickinger, Annette G. "Drug delivery and release systems for targeted tumor therapy." Journal of Peptide Science 21(3):186-200, (Year: 2015).
Hasan, Mahmud et al. "Drug conjugates—an emerging approach to treat breast cancer." Pharmacol Res Perspect. 6 (4):1-17, (Year: 2018).
Merk, Daniel et al. Drug Selectivity: an evolving concept in medicinal chemistry. John Wiley & Sons, 1st ed., Chapter 8, pp. 207-245, (Year: 2018).

* cited by examiner

*Primary Examiner* — Sarah Pihonak
(74) *Attorney, Agent, or Firm* — SALIWANCHIK, LLOYD & EISENSCHENK

(57) ABSTRACT

The present invention relates to a compound comprising a cisplatin component and a eugenol component. The present invention further relates to a synthesis method of said compound, pharmaceutical compositions comprising the compound and its medical uses. The present invention further relates to a method of treatment of cancer.

2 Claims, 13 Drawing Sheets

$R^1 = CH_2\text{-}CH{=}CH_2,\ CH{=}CH\text{-}CH_3$
$R^2 = OCH_3,\ OCH_2\text{-}CH_3$ Formula Weight = 427.79118

Formula Weight = 375.3071114

CISPLATIN ANALOGUE WITH POTENT ANTI-CANCER EFFECTS AND SYNTHESIS THEREOF

CROSS REFERENCE TO A RELATED APPLICATION

This application is a Divisional Application of U.S. Ser. No. 17/877,339, filed Jul. 29, 2022, which is incorporated herein in it's entirety.

FIELD OF THE INVENTION

The present invention relates to a compound comprising a cisplatin component and a eugenol component. The present invention further relates to a synthesis method of said compound, pharmaceutical compositions comprising the compound and its medical uses. The present invention further relates to a method of treatment of cancer.

BACKGROUND OF THE INVENTION

Cisplatin (cis-diamminedichloroplatinum II) is a well-known metal-based DNA damaging chemotherapeutic drug, which has been used for the treatment of different types of cancer. Indeed, cisplatin is effective against various types of tumors, including carcinomas, lymphomas, and sarcomas (Tchounwou et al., 2021). Unfortunately, even low and non-toxic concentrations of cisplatin in the serum could be toxic in the kidneys. Indeed, 30-40% of cisplatin-treated patients develop acute kidney injury (Volarevic et al., 2019). To overcome these clinical limitations, different cisplatin analogues were synthesized and are currently used for the treatment of various types of tumors. These include carboplatin and oxaliplatin, which showed efficiency and less toxicity (Desoize et al., 2002; Ali et al., 2013).

We have recently shown that eugenol, a phenolic natural compound present essentially in clove oil with anti-cancer potential, can potentiate the effect of cisplatin against breast cancer and ovarian cancer cells both in vitro and in vivo (Islam et al., 2018; Islam et al., 2019).

Interestingly, while the simultaneous combination of cisplatin with eugenol was very effective against breast cancer cells, it was ineffective and generated an antagonistic effect against ovarian cancer cells (Islam et al., 2018; Islam et al., 2019). In fact, only the sequential combination (cisplatin followed by eugenol) was effective against ovarian cancer cells (Islam et al., 2019).

Thus, there is a need for developing further cisplatin analogues with higher efficiency and less side effects.

There is also a need to have effective drugs against resistant as well as recurrent tumors, which are the most resistant ones. There is also a further need for the treatment of deadly metastatic tumors.

SUMMARY OF THE INVENTION

According to the present invention this object is solved by a compound comprising a cis-diamminedichloroplatinum II component (cisplatin component) and a 2-methoxy-4-(prop-2-en-1-yl)phenol component (eugenol component) which are covalently connected via a linker.

According to the present invention this object is solved by a method of synthesizing the compound of the present invention comprising:

(1) adding eugenol and a base, preferably NaOH, to water; and optional, stirring the mixture;

(2) adding cisplatin to the mixture of (1); and optional, stirring the mixture;

(3) obtaining the compound, which is preferably a solid, which is more preferably washed and dried.

According to the present invention this object is solved by a pharmaceutical composition comprising:

(a) a compound of the present invention or a compound obtained by the method of the present invention;

(b) optional, pharmaceutically acceptable excipient(s) or carrier.

According to the present invention this object is solved by providing the compound of the present invention or the compound obtained by the present invention or the pharmaceutical composition of the present invention for use in medicine.

According to the present invention this object is solved by providing the compound of the present invention or the compound obtained by the present invention or the pharmaceutical composition of the present invention for use in a method of treatment of cancer.

According to the present invention this object is solved by a method of treatment of cancer, comprising administering to a subject in need thereof a therapeutically amount of a compound of the present invention or a compound obtained by the method of the present invention or the pharmaceutical composition of the present invention.

In yet a further aspect of the present invention, this object is solved by the use of the compound in accordance with the present invention for the manufacture of a medicament for the treatment of cancer.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "18 to 30" should be interpreted to include not only the explicitly recited values of 18 to 30, but also include individual values and sub-ranges within the indicated range. Thus, included in this numerical range are individual values such as 18, 19, 20, 21 . . . 29, 30 and sub-ranges such as from 20 to 28, 20 to 25, 21 to 24, 7 to 9 etc. This same principle applies to ranges reciting only one numerical value, such as below 25". Furthermore, such an interpretation should apply regardless of the breadth of the range or the characteristics being described.

Cisplatin Analogues

As outlined above, the present invention provides compounds a cis-diamminedichloroplatinum II component (cisplatin component) and a 2-methoxy-4-(prop-2-en-1-yl)phenol component (eugenol component).

The compound of the present invention comprises a cisplatin component and an eugenol component, which are covalently connected via a linker.

Cisplatin is a chemotherapy medication used to treat a number of cancers. Other names are cisplatinum, platamin, neoplatin, cismaplat, cis-diamminedichloroplatinum II (CDDP). The IUPAC name is: (SP-4-2)-diamminedichloridoplatinum(II). The sum formula is $[Pt(NH_3)_2Cl_2]$ or $PtCl_2(NH_3)_2$. Cisplatin has the formula:

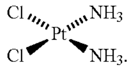

A "cisplatin component" as used herein refers to cisplatin and to cisplatin analogues with the sum formula $PtCl(NH_3)_2$.

Eugenol is an allyl chain-substituted guaiacol, a member of the allylbenzene class of chemical compounds. It is a colorless to pale yellow, aromatic oily liquid extracted from certain essential oils especially from clove, nutmeg, cinnamon, basil and bay leaf. It is present in concentrations of 80-90% in clove bud oil and at 82-88% in clove leaf oil. The preferred IUPAC name is 2-methoxy-4-(prop-2-en-1-yl) phenol. The sum formula is $C_{1-}H_{12}O_2$. Eugenol has the formula:

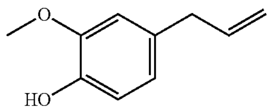

.

A "eugenol component" as used herein refers to eugenol and to eugenol analogues with the sum formula $C_{10}H_{11}O_2$.

The compound of the present invention preferably has the general formula I

Cis-L-Eug (I)

wherein

Cis is the cisplatin component,

L is a linker, and

Eug is the eugenol component.

A "linker" as used herein is preferably a covalent bond between the cisplatin component and the eugenol component.

The compound of the present invention can be obtained by reacting eugenol with cisplatin, preferably in presence of a base.

The compound of the present invention can be called eugenoplatin (EP). The compound of the present invention is an anti-cancer compound.

The compound of the present invention has preferably the sum formula $PtCl(NH_3)_2C_{10}H_{11}O_2$.

The compound of the present invention also comprises the pharmaceutically active salts.

The compound of the present invention has preferably the formula

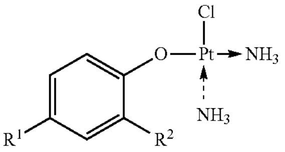

wherein $R^1$ is $-CH_2-CH=CH_2$ or $-CH=CH-CH_3$, and $R^2$ is $-OCH_3$ or $-OCH_2-CH_3$, or a pharmaceutically active salt thereof.

In one embodiment, the compound of the present invention has the formula

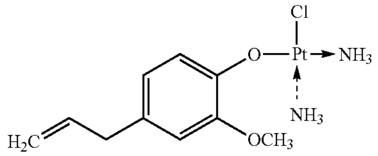

or a pharmaceutically active salt thereof.

Synthesis Method

As outlined above, the present invention provides a method of synthesizing the compound of the present invention.

Said method comprises the following steps (1) adding eugenol and a base, preferably NaOH, to water;
   and optional, stirring the mixture;

(2) adding cisplatin to the mixture of (1);
   and optional, stirring the mixture;

(3) obtaining the compound, which is preferably a solid, which is more preferably washed and dried.

Step (1)

In step (1), eugenol and a base are added to water.

The base is preferably NaOH or KOH.

Preferably, eugenol and the base have a similar molarity/are added in a ratio of about 1:1 by molarity.

The mixture of eugenol and the base is preferably stirred, such as for about 1 to 4 hours, such as about 2 hours, at a temperature from about 15 to about 25° C., such as at room temperature.

Step (2)

In step (2), cisplatin is added to the mixture of (1).

Preferably, cisplatin and eugenol and the base have a similar molarity/are added in a ratio of about 1:1:1 by molarity.

The mixture of eugenol and the base and cisplatin is preferably stirred, such as for about 18 to 30 hours, such as about 24 hours, at a temperature from about 15 to about 25° C., such as at room temperature.

Step (3)

In step (3), the compound is obtained.

The compound obtained in step (3) is preferably a solid.

The solid is preferably washed and dried.

For example, a solid is formed and in addition to that a (yellow) solution. The (yellow) solution is removed by centrifugation and the sticky solid is washed three times with methanol, and is isolated by centrifugation, and then dried under vacuum.

Preferably, the obtained compound is characterized by HPLC analysis and/or mass spectroscopy.

Pharmaceutical Composition and Medical Uses

As outlined above, the present invention provides a pharmaceutical composition comprising:

(a) a compound of the present invention or a compound obtained by the method of the present invention;

(b) optional, pharmaceutically acceptable excipient(s) or carrier.

As outlined above, the present invention provides the compound of the present invention or the compound obtained by the method of the present invention or the pharmaceutical composition of the present invention for use in medicine.

The compounds of the present invention show potent anti-cancer activities against various types of cancer cells. Therefore, the compounds have great therapeutic value for the treatment of different types of tumors.

As outlined above, the present invention provides the compound of the present invention or the compound obtained by the method of the present invention or the pharmaceutical composition of the present invention for use in a method of treatment of cancer.

Preferably, the cancer is breast cancer, ovarian cancer, osteosarcoma, colorectal cancer, glioblastoma, leukemia, lymphoma, lung cancer or thyroid cancer.

In one embodiment, the compound of the present invention or the compound obtained by the 30 method of the present invention or the pharmaceutical composition of the present invention is used in combination with at least one further anticancer treatment, such as chemotherapy and/or immunotherapy.

In one embodiment, where the use is in combination with chemotherapy, the chemotherapeutic agent can be docetaxel, paclitaxel or doxorubicin.

In one embodiment, where the use is in combination with immunotherapy, different immunotherapeutic molecules can be used.

In a further aspect, the present invention also relates to the use of the compound in accordance with the present invention for the manufacture of a medicament for the treatment of cancer.

Treatment Method

As outlined above, the present invention provides a method of treatment of cancer.

Said method comprises administering to a subject in need thereof a therapeutically effective amount of a compound of the present invention or a compound obtained by the method of the present invention or the pharmaceutical composition of the present invention.

A "therapeutic amount" or a "therapeutically effective amount" of a compound of the present invention refers to the amount which has to be administered to a subject in need thereof in order to achieve a desired therapeutic result or outcome. The skilled artisan will be able to determine said therapeutically effective amount and the suitable administration regimen.

Preferably, the cancer is breast cancer, ovarian cancer, osteosarcoma, colorectal cancer, glioblastoma, leukemia, lymphoma, lung cancer or thyroid cancer.

In a preferred embodiment, the administration is via infusion.

In one embodiment, the method of the present invention is carried out in combination with at least one further anticancer treatment, such as chemotherapy and/or immunotherapy.

Further Description of Preferred Embodiments

Abstract

The invention relates to the synthesis of a cisplatin analogue called eugenoplatin consisting of an association between cisplatin ($PtCl_2$ $(NH_3)_2$) and eugenol ($C_{10}H_{12}O_2$). The novel molecule $PtCl(NH_3)_2C_{10}H_{11}O_2$ shows potent anti-cancer activities against various types of cancer cells.

Therefore, the new compound has great therapeutic value for the treatment of different types of tumors. The steps of the obtention of this anti-cancer cisplatin analogue are as follows:

1. Synthesis of the combined cisplatin and eugenol molecule (eugenoplatin, EP);
2. HLPC and MS characterization of eugenoplatin;
3. Elucidation of the anticancer properties of eugenoplatin;
4. Experiments that show that eugenoplatin targets cancer stem cells; and
5. Experiments that show that eugenoplatin introduces DNA damage in human cells.

Results

1. Synthesis of the Combined Cisplatin and Eugenol Molecule (Eugenoplatin, EP)

Eugenol (50.0 mg at 0.304 mM) and NaOH (320 µl of 1 M.0 M NaOH at 0.320 mM) were added to 2.0 mL water, and the mixture was stirred at room temperature for 120 mM. Subsequently, cisplatin (92.0 mg at 0.306 mM) was added to the eugenol solution and the mixture was stirred at room temperature for 24 h, the next day a yellow solution was formed in addition to a sticky solid. The yellow solution was removed by centrifugation and the sticky solid was washed three times with 1.0 mL methanol, and was isolated by centrifugation, and then dried under vacuum.

2. HLPC and MS Characterization of Eugenoplatin

The formed product was first analyzed by HPLC using analytical C18 Columns and dual Detection UV Detector. FIG. 1 shows the presence of a 100% pure single peak with no other peaks and no starting material, both at UV=254 nm and at UV=220 nm. The novel peak (molecule) had a retention time of 5 mM, while the retention time of eugenol and cisplatin are 3 min and 16 min, respectively. This suggests the formation of a third/new molecule with new physical features and an expected molecular weight of 428.0 with the most possible structure as shown in FIG. 2B. The Mass Spectroscopy analysis showed one main peak of MS+1=452 (FIG. 2A), which corresponds to the molecule plus sodium (428.0+23=451) (FIG. 2B), and one fragment of MS+1=375, which corresponds to the structure shown in FIG. 2C. v 3. Anticancer Effects of Eugenoplatin on Different Cancer Cell Lines in Vitro 3.1 Cytotoxicity Using the widely used cytotoxicity assay (WST1) we first show that eugenoplatin is highly toxic against cancer cells from different types: breast cancer, ovarian cancer, osteosarcoma, colorectal cancer, glioblastoma, and leukemia with different $IC_{50}$ (Table 1). Table 1 shows also that the cytotoxic effect of eugenoplatin is higher than that of cisplatin against breast cancer, osteosarcoma and glioblastoma cells. Eugenoplatin showed also higher toxicity against colorectal cancer, ovarian cancer and leukemia cells than oxaloplatin, carboplatin and cytarabine (Ara-C), respectively (FIGS. 3A-3C and Table 1).

TABLE 1

| Cancer Type | Cell lines | Eugenoplatin | Cisplatin | Carboplatin | Oxaliplatin | Cytarabine Ara-C |
|---|---|---|---|---|---|---|
| Breast | MDA-MB-231 | 1.24 ± 0.11 | 22.83 ± 2.13 | — | — | — |
| Osteosarcoma | MG-64 | 0.88 ± 0.16 | 26 ± 4 | — | — | — |
| Lung | H-1937 | 2.72 ± 0.19 | 67.75 ± 7.75 | — | — | — |
| Glioblastoma | A1235 | 4.58 ± 0.08 | 55.75 ± 18.25 | — | — | — |
| Thyroid | Cal62 | 1.45 ± 0.28 | 25.67 ± 2.19 | — | — | — |
| Ovarian | OV-2774 | 1.83 ± 0.35 | — | 53.33 ± 0.67 | — | — |
| Colon | HCT-116 | 2.2 ± 0.03 | — | — | 3.17 ± 0.52 | — |
| AML | THP-1 | 0.3 ± 0.25 | — | — | — | 3 ± 0.05 |

3.1 The Cytotoxic Effect of Eugenoplatin is Specific to Cancer Cells

The specificity of anti-cancer drugs is of great importance to limit the side effects of these molecules. Therefore, we tested the cytotoxic effects of eugenoplatin on different types of normal cells. FIG. 4 shows that eugenoplatin has only marginal cytotoxicity against breast epithelial cells (MCF-10A), and blood cells (PBMCs from 3 healthy donors). Indeed, eugenoplatin at 5 μM killed only 40% and less than 20% in MCF-10A cells and blood cells, respectively.

3.1 Eugenoplatin Promotes Apoptosis in Cancer Cells

We have used the annexinV/propidium iodide-flow cytometry technique to show that, like cisplatin, eugenoplatin promotes mainly apoptosis in both breast cancer (MDA-MB-231) as well as ovarian cancer (OV-2774) cells (FIGS. 5A and 5B). Indeed, at 3 μM and 5 μM of eugenoplatin the proportion of apoptotic cells reached 68% in breast cancer and ovarian cancer cells, respectively (FIGS. 5A and 5B). This was confirmed in different cancer cell lines using immunoblotting and antibodies specific for the pro-apoptotic protein PARP, caspase-3, caspase-9.

FIG. 5C shows that eugenoplatin increased the level of cleaved PARP, caspase-3 and caspase-9 in breast cancer (MDA-MB-231), ovarian cancer (OV-2774), osteosarcoma (MG-64), colon cancer (HCT-116), lung cancer (H-1937), glioblastoma (A1235) and leukemia cells (THP-1). This effect was more efficient than that of cisplatin, carboplatin or oxaliplatin on breast cancer and osteosarcoma cells, ovarian cancer cells, and colorectal cancer cells, respectively (FIG. 5C).

4. Eugenoplatin Targets Cancer Stem Cells

It is well known that cancer stem cells are the most resistant type of cells, which are responsible for recurrence and metastasis (Garcia-Mayea et al., 2020). Therefore, we decided to investigate the effect of eugenoplatin on the self-renewal ability and stemness capacity of cancer cells. To this end, cancer cells were first either sham-treated (DMSO) or challenged with eugenoplatin (3 μM) for 24 h, and then were incubated in 96 well ultra-low attachment plates in the presence of stem cells culture medium. After 10 days, the formed spheroids with a dimeter ≥100 μm were counted (FIG. 6A). FIG. 6B shows that eugenoplatin treatment reduced by 3-fold and the capacity of MDA-MB-231 and MG-64 cells to form tumorespheres, respectively. Furthermore, tumorespheres were first formed, and then they were either sham-treated (DMSO) or challenged with eugenoplatin (3 μM) or cisplatin (50 μM) for 24 h and the cytotoxicity was assessed using WST1. FIG. 6C shows that while the proportion of survival CSC was reduced to 70% (MDA-MB-231) and 50% (MG-64) upon treatment with eugenoplatin, it was not affected by cisplatin treatment. This indicates that while cancer stem cells are not sensitive to cisplatin, they showed sensitivity to eugenoplatin.

6. Eugenoplatin Promotes DNA Damage in Human Fibroblast Cells

Since cisplatin is a DNA damaging chemotherapeutic drug, we investigated whether eugenoplatin can also promote DNA damage in cells. To this end, human fibroblast cells (HFSN1) were either sham-treated (DMSO) or challenged with cisplatin (50 μM) or eugenoplatin (3 μM) for 24 h, and then the level of the DNA damage sensing protein (γ-H2AX) was assessed by immunofluorescence. While no γ-H2AX immunostaining was detected in the control cells, a strong nuclear staining was observed in response to cisplatin, confirming cisplatin-dependent induction of DNA damage (FIG. 7A). Interestingly, cells treated with eugenoplatin also showed γ-H2AX immunostaining at the nucleus (FIG. 7A). This suggests that eugenoplatin can also induce DNA damage in human cells. To confirm this, we assessed the level of the phosphorylated form of p53 (P.p53) in eugenoplatin-treated cells. FIG. 7B shows strong increase in the level of P.p53 in a time-dependent manner. This was accompanied by a late increase in the level of the p53 target p21 (FIG. 7B). These results show eugenoplatin-dependent induction of DNA damage in human cells.

The following examples and drawings illustrate the present invention without, however, limiting the same thereto.

(2A) Mass Spectroscopy analysis of the newly synthesized eugenoplatin molecule.

(2B) The molecular formula and the corresponding weight of eugenoplatin.

(2C) The molecular formula and the weight of the molecule corresponding to the peak 375.0814.

Figure 1:
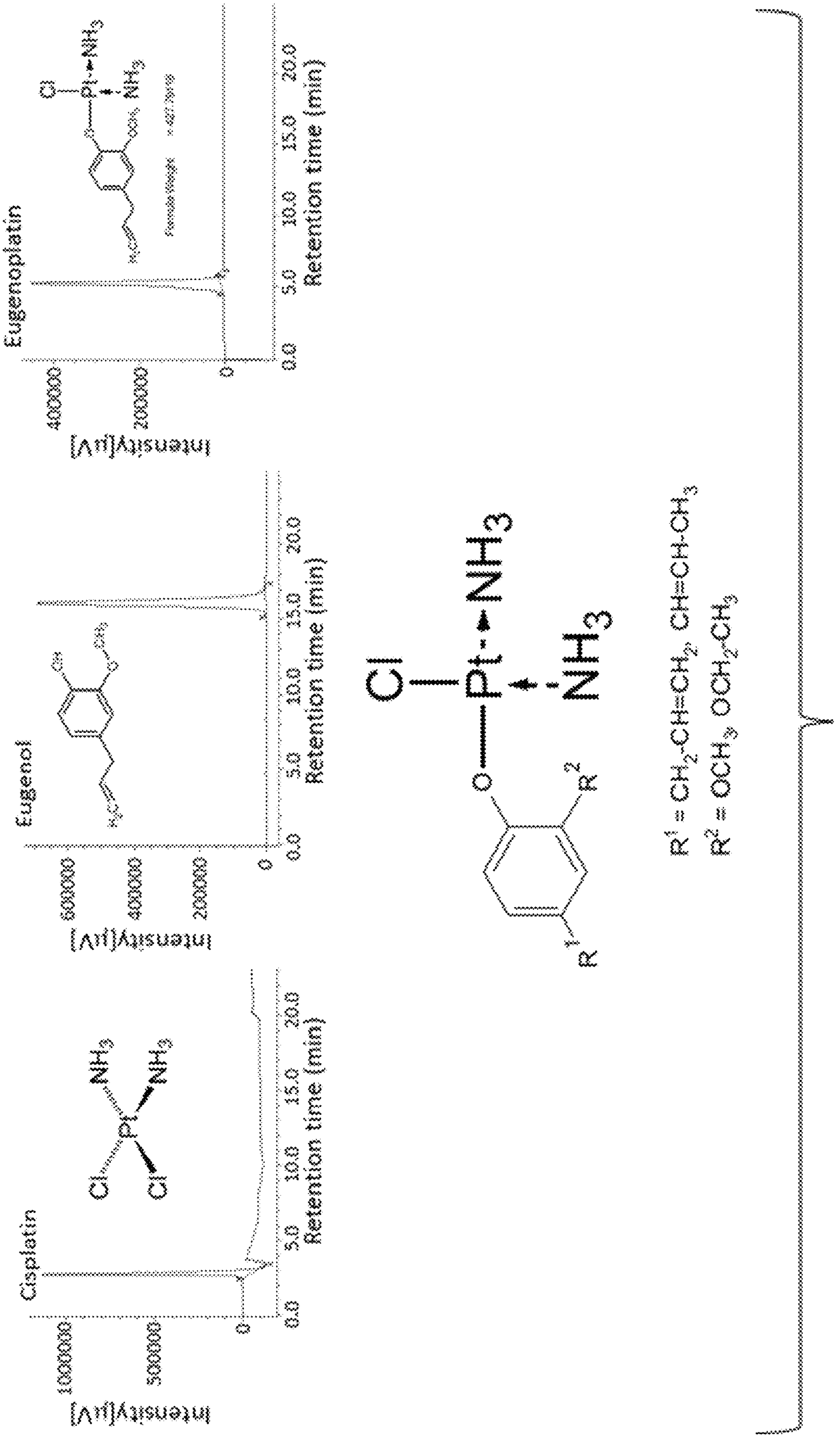
FIG. 1. HPLC analysis of the three molecules: cisplatin, eugenol and eugenoplatin using analytical C18 Columns and dual Detection UV Detector.
Figure 2A:
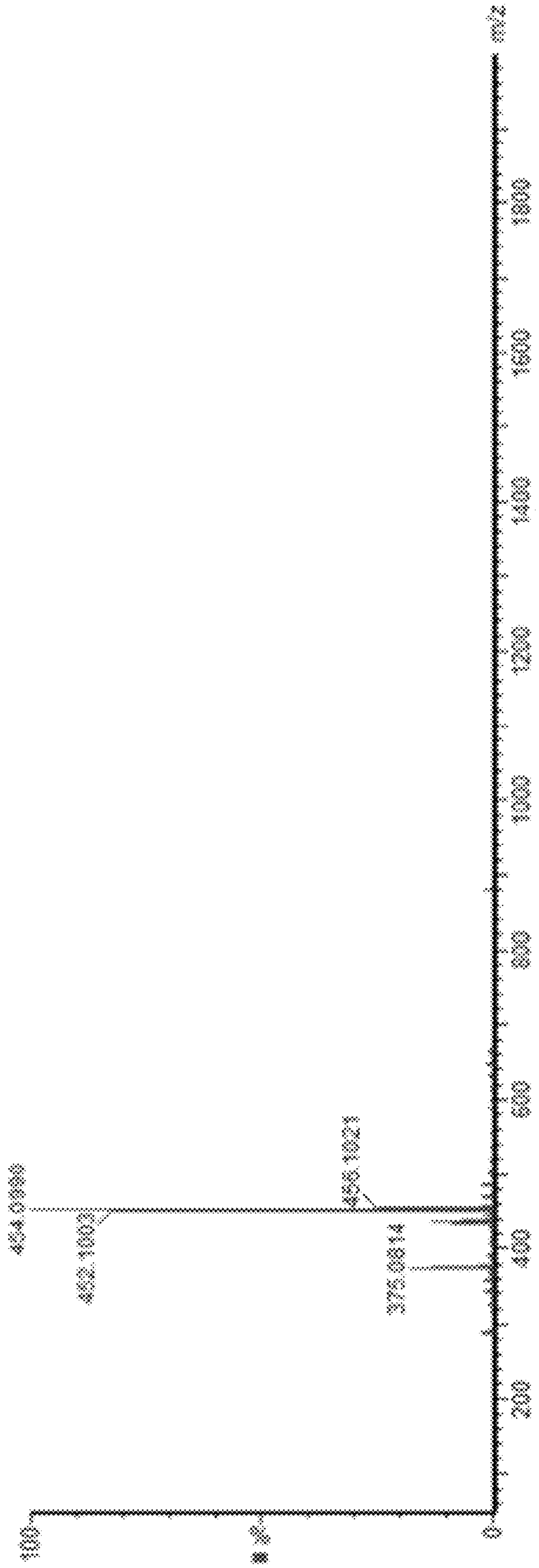
FIGS. 2A-2C. Mass Spectroscopy analysis of eugenoplatin.
Figure 2B:
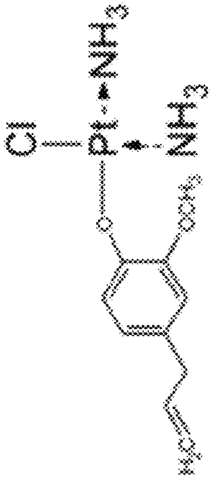
Figure 2C:
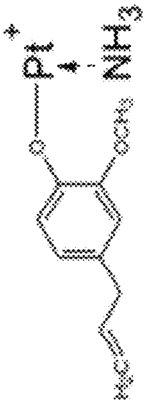
Figure 3A:
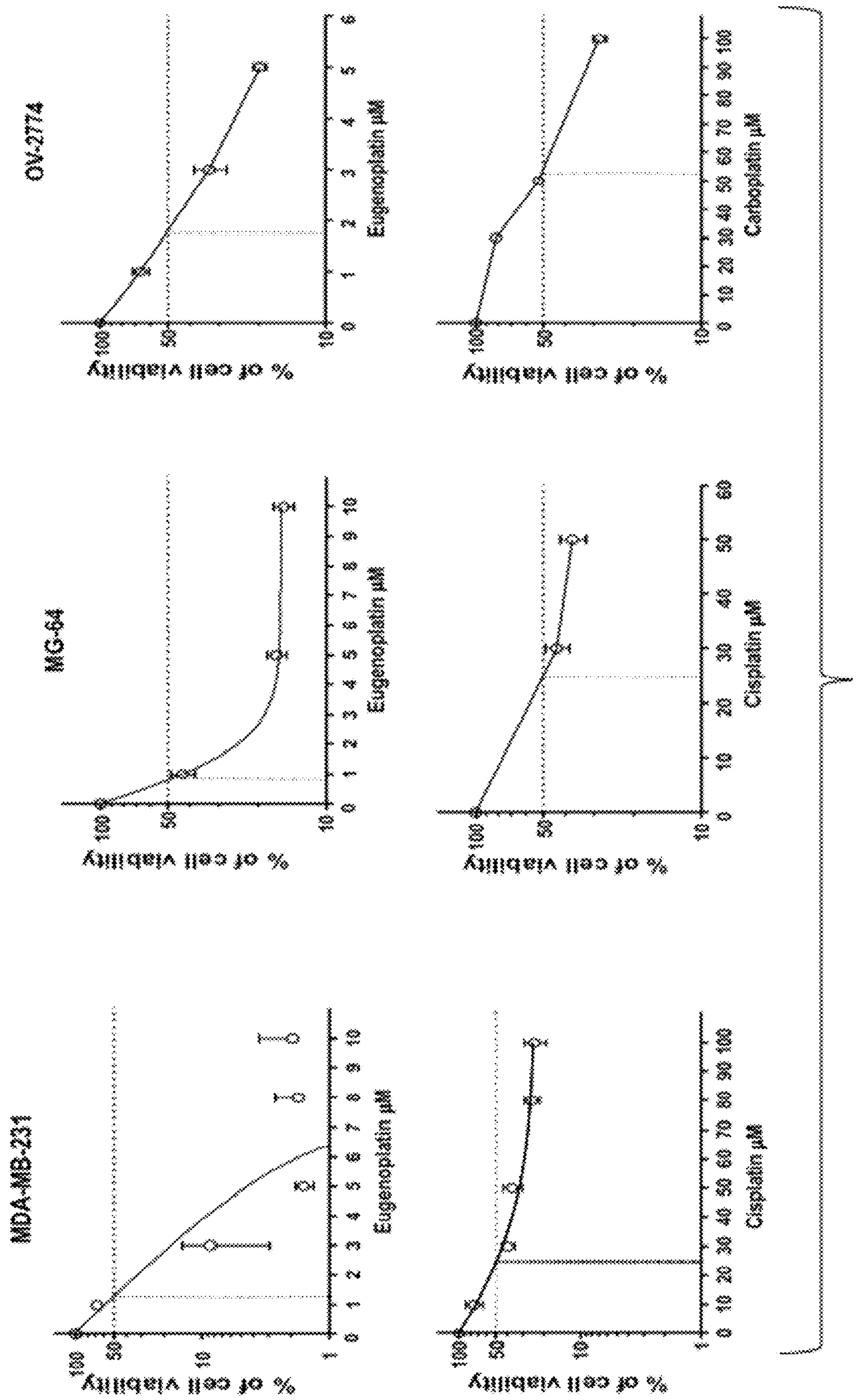
Figure 3B:
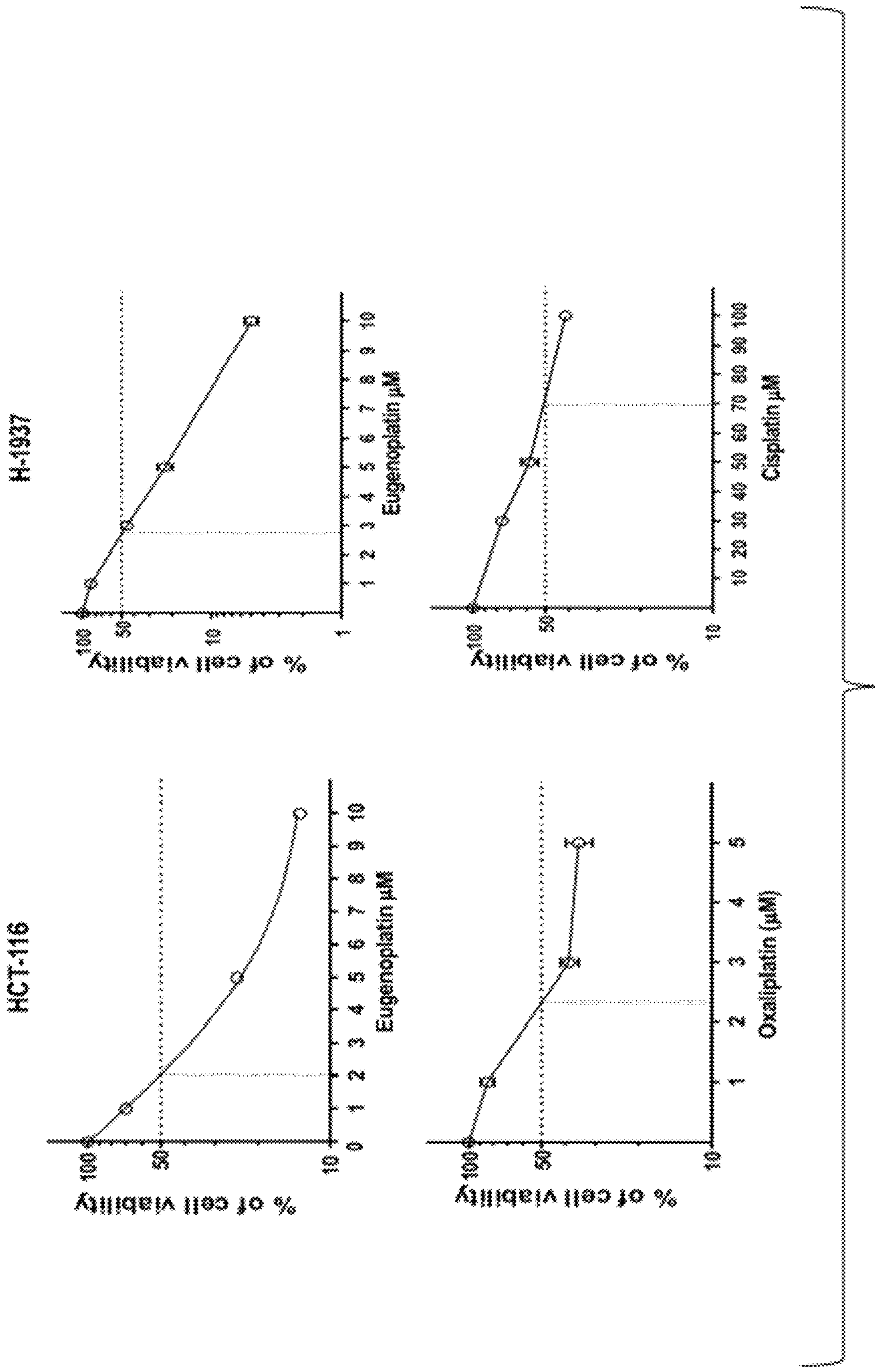
Figure 3C:
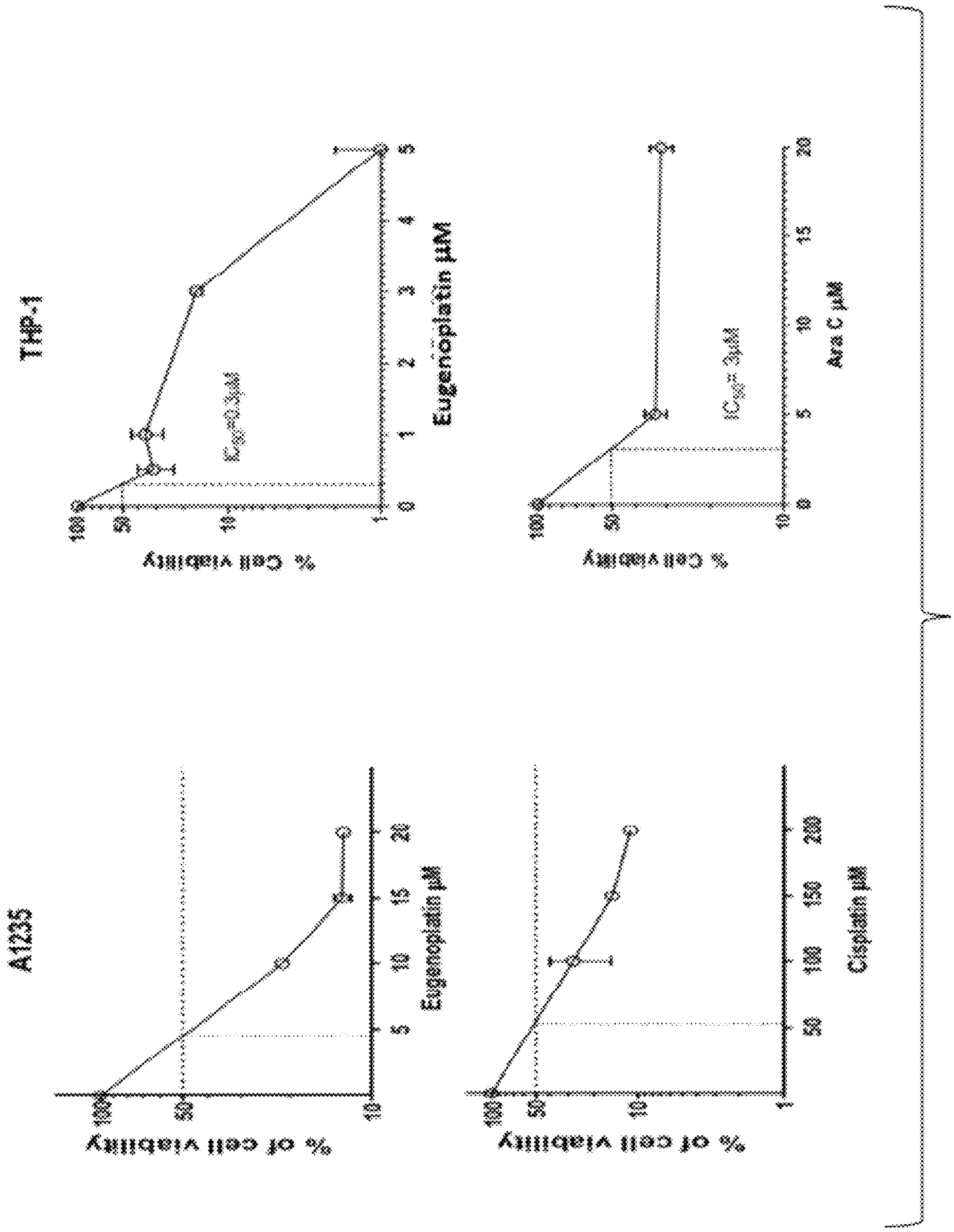

FIGS. 3A-3C. Eugenoplatin is highly cytotoxic against various types of cancer.

The indicated cells, namely MDA-MB-231, MG-64, and OV-2774 in FIG. 3A, HCT-116, and H-1937 in FIG. 3B, A1235 and THP-1 in FIG. 3C, were treated with the indicated concentrations of eugenoplatin or cisplatin, carboplatin, oxaliplatin, AraC as indicated, and then the cytotoxic effects of these drugs was assessed by the WST1 assay. Error bars represent mean±S. D (n=3). The $IC_{50}$ are indicated by lines in dots.

Figure 4:
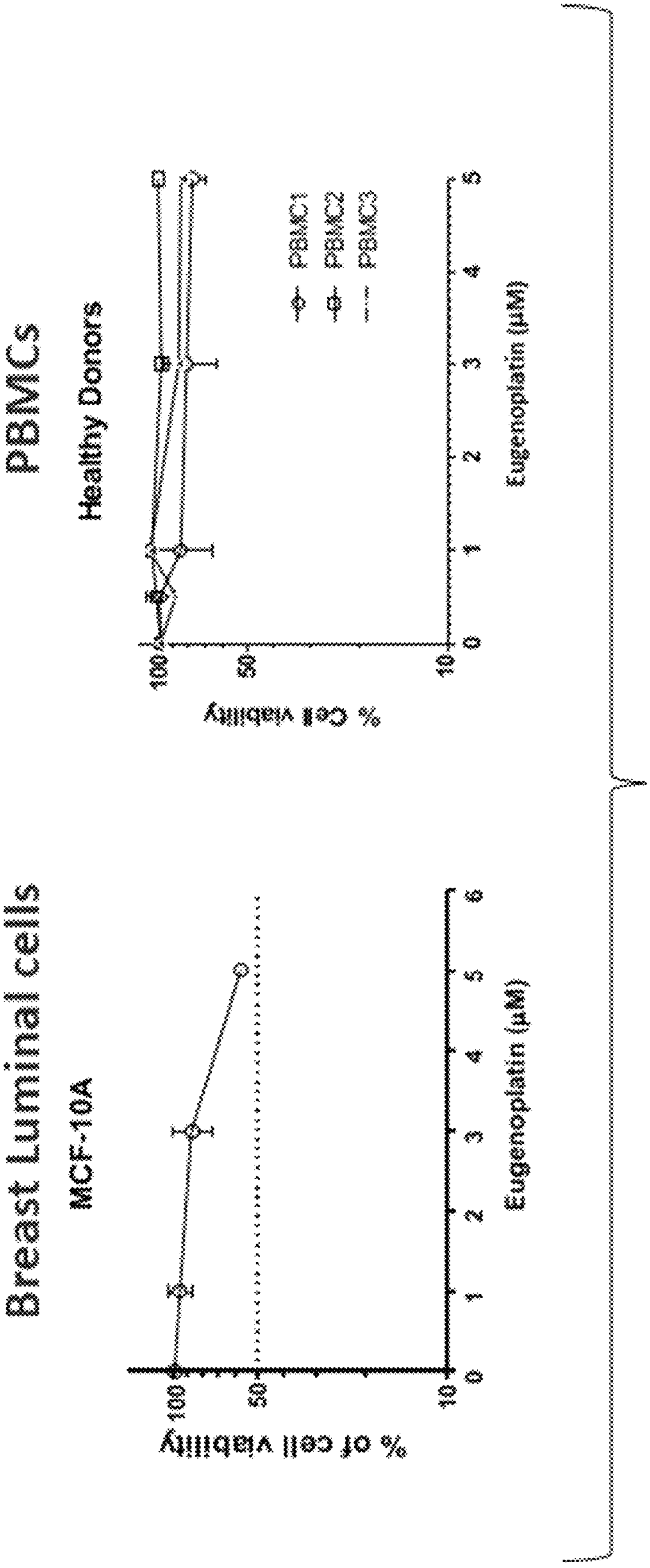

FIG. 4. Eugenoplatin is not cytotoxic against normal human cells.

Breast luminal cells (MCF-10A) and blood cells (PBMCs of healthy donors') were treated with the indicated concentrations of eugenoplatin, and then the cytotoxic effect was assessed by the WST1 assay. Error bars represent mean±S. D (n=3).

Figure 5A:
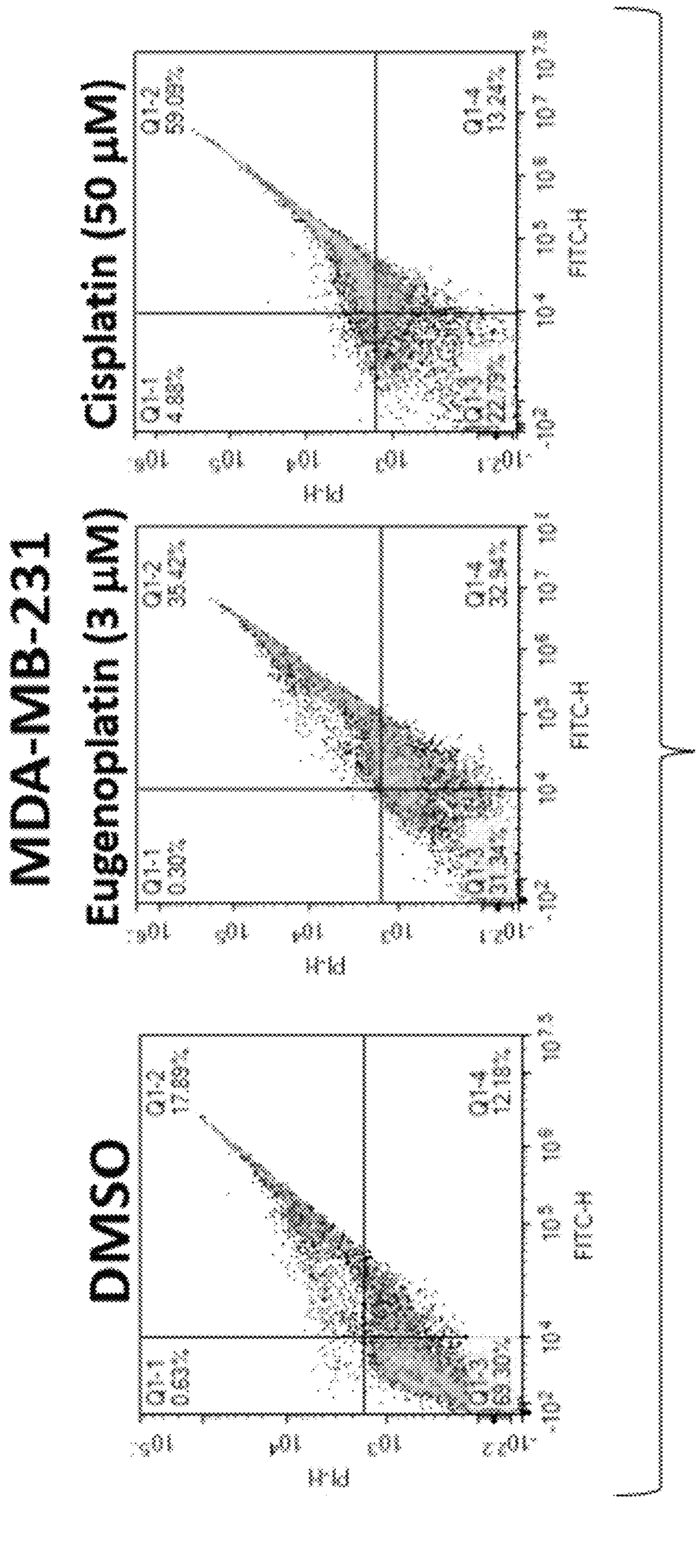
Figure 5B:
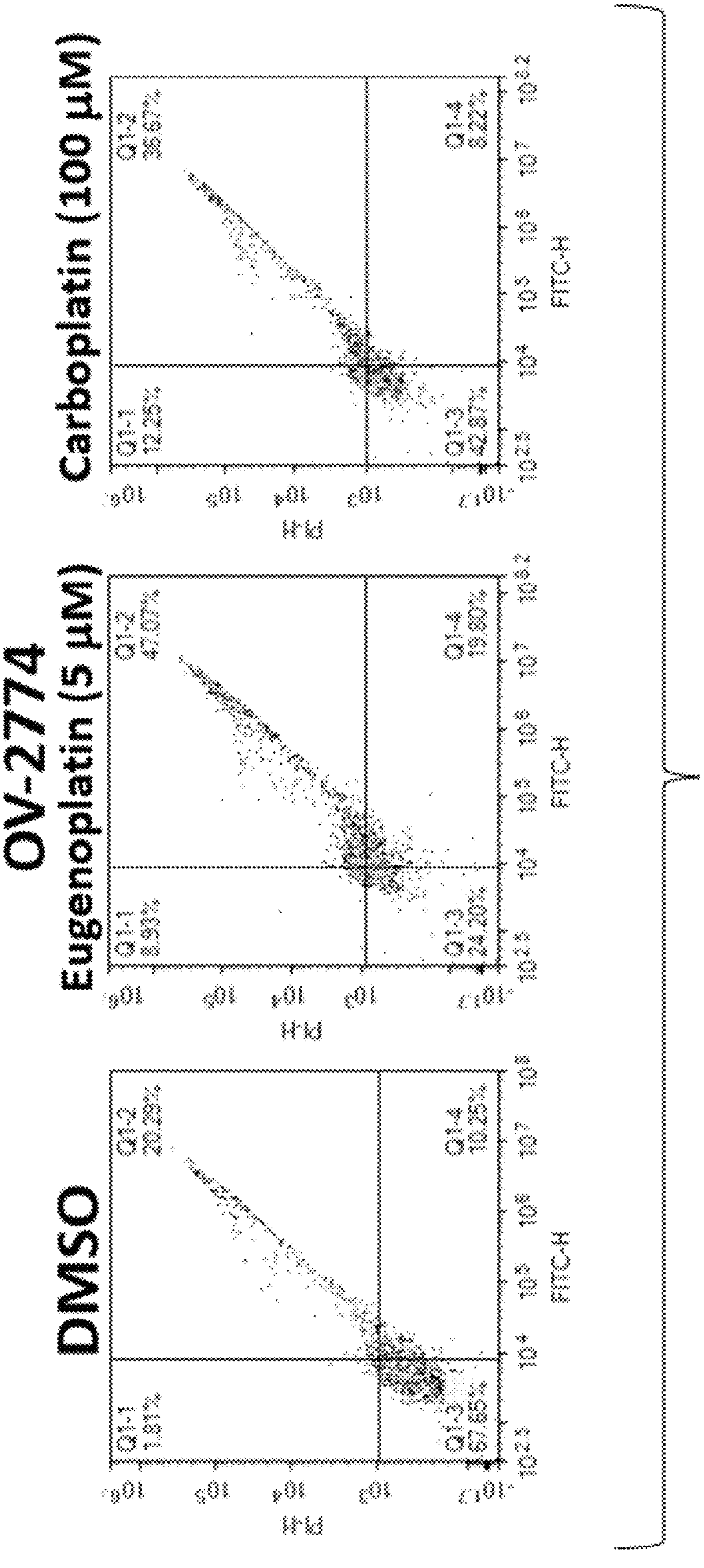
Figure 5C:
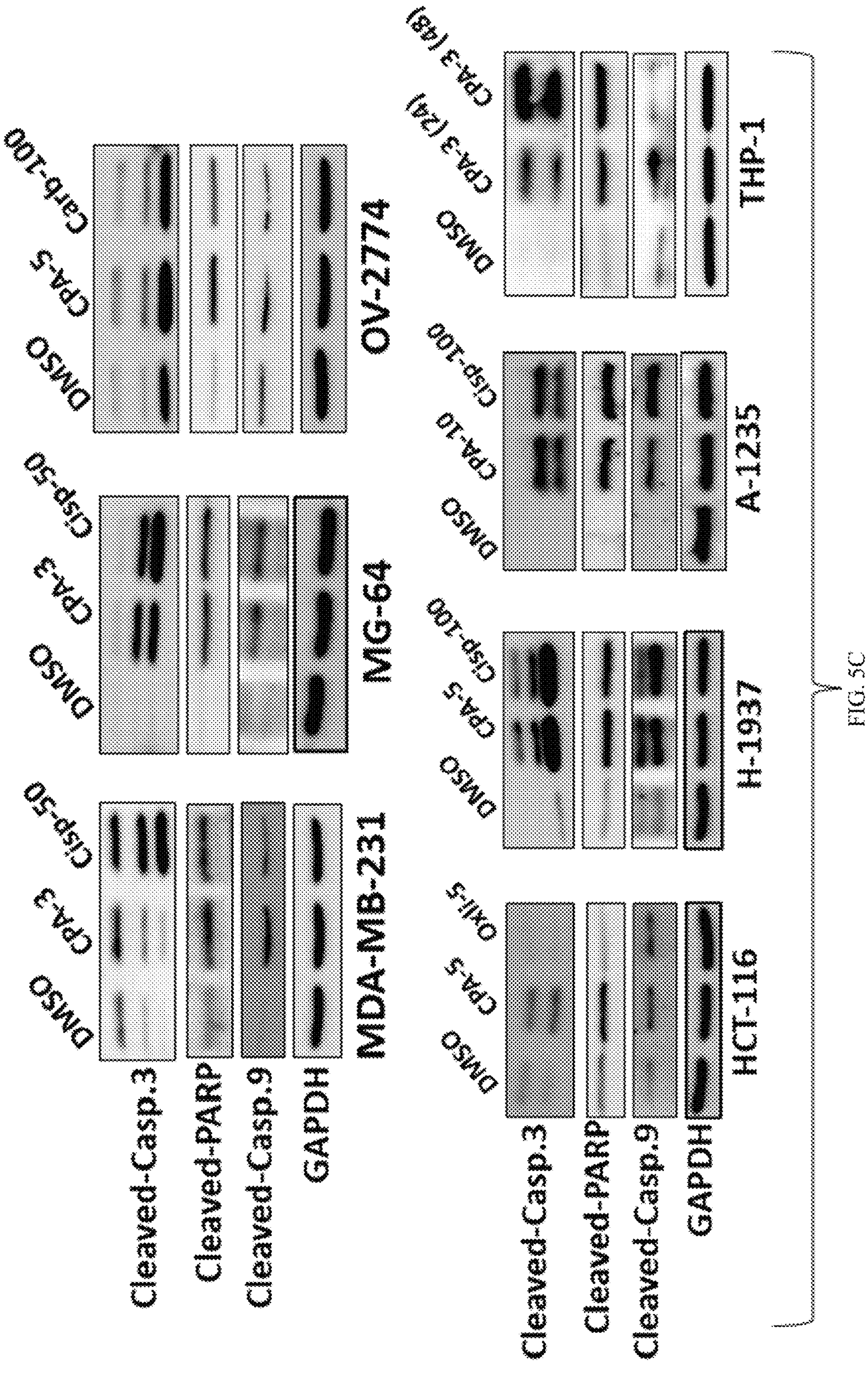

FIGS. 5A-5C. Eugenoplatin promotes apoptosis in tumor cells from various types of cancer.

(5A) and (5B) MDA-MB-231 and OV-2774 cells, respectively, were treated with eugenoplatin or cisplatin/carboplatin as indicated. Cell death was then assessed by annexinV/propidium iodide-associated with flow cytometry.

(5C) The indicated cells, namely MDA-MB-231, MG-64, OV-2774, HCT-116, H-1937, A1235 and THP-1, were treated as indicated, and then whole cell lysates were prepared and used for immunoblotting analysis using antibodies against the indicated proteins.

Figure 6A:
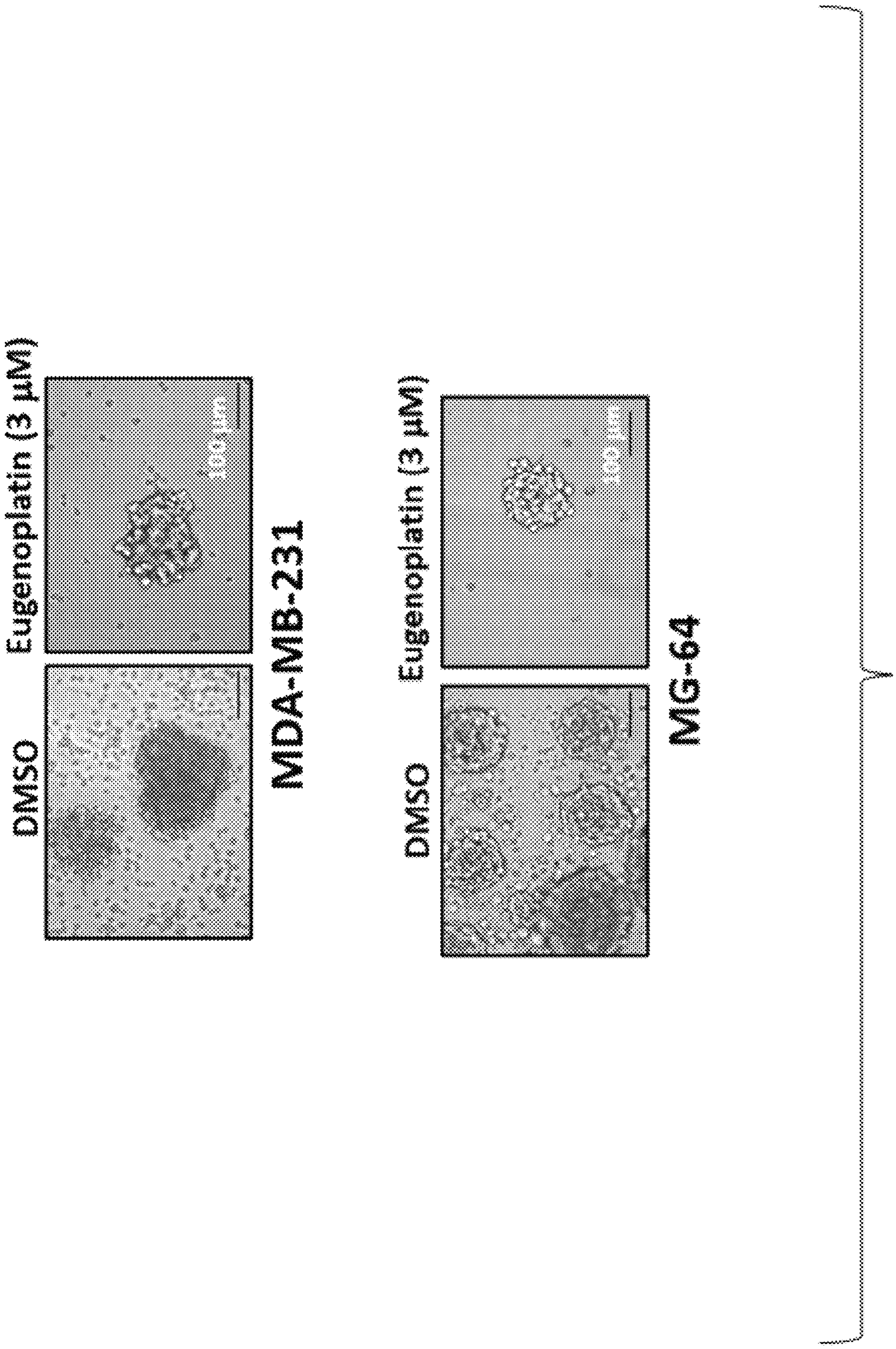
Figure 6C:
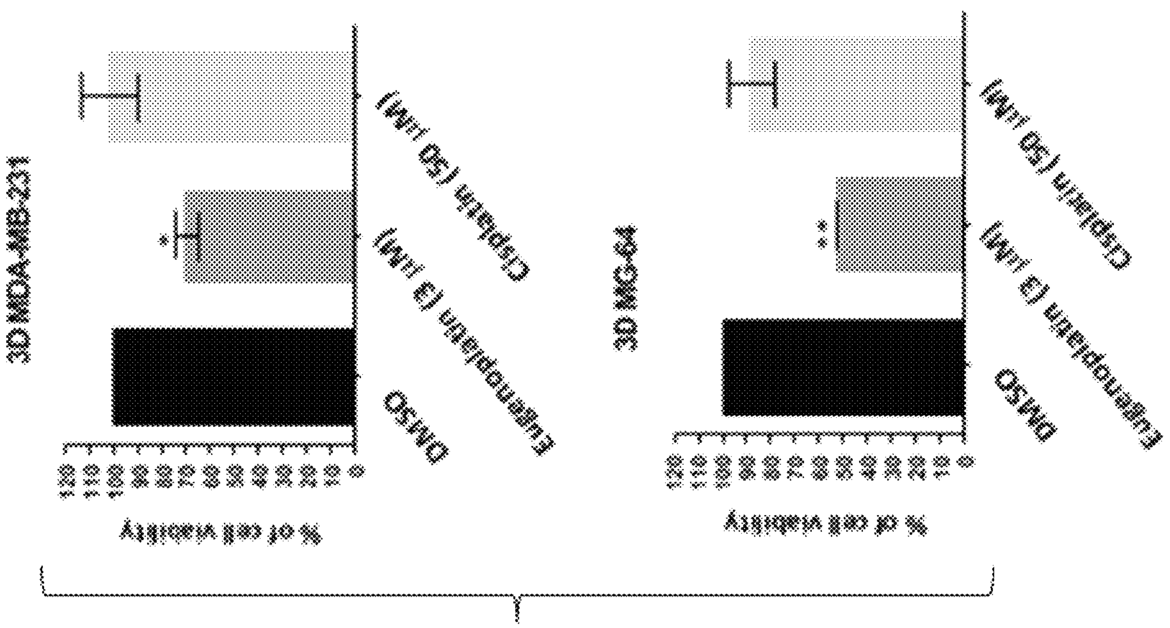
Figure 6B:
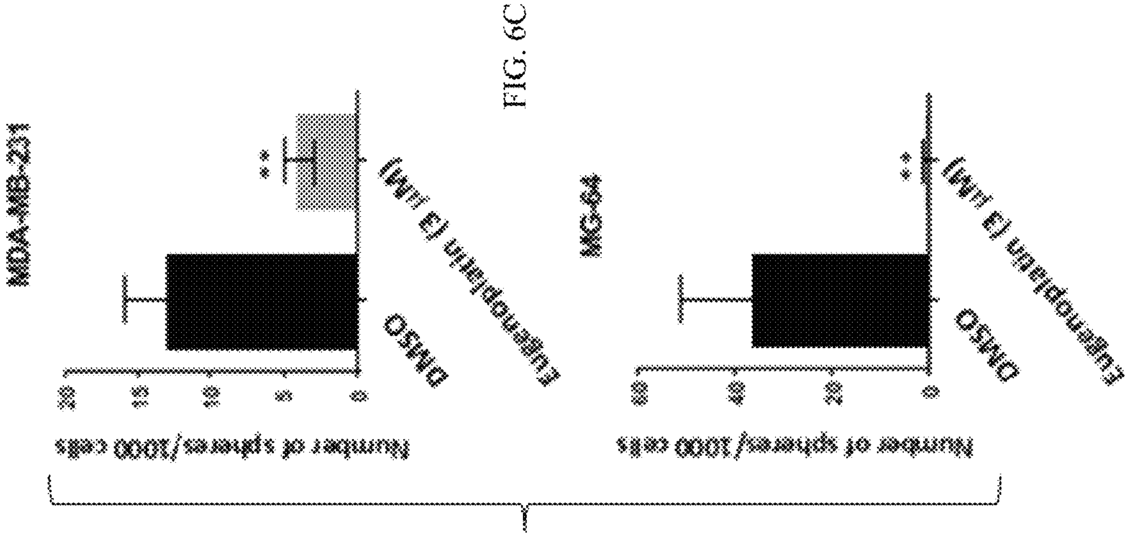

FIGS. 6A-6C. Eugenol targets cancer stem cells.

Cells (2000) were first either sham-treated (DMSO) or challenged with eugenoplatin (3 μM) for 24 h, and then were incubated in 96 well ultra-low attachment plates in the presence of stem cells culture medium. After 10 days, the formed spheroids with a dimeter ≥100 μM were counted.

(6A) Images of the formed spheroids.

(6B) Histogram showing the number of formed spheroids. Error bars represent mean±S. D (n=3).

(6C) Cells were first incubated in 96 well ultra-low attachment plates in the presence of stem cells culture medium. After 10 days, the formed spheroids with a dimeter ≥100 μM were either sham-treated (DMSO) or challenged with eugenoplatin (3 μM) or cisplatin (50 μM) for 24 h and the cytotoxicity was assessed using WST1. Error bars represent mean±S. D (n=3).

Figure 7A:
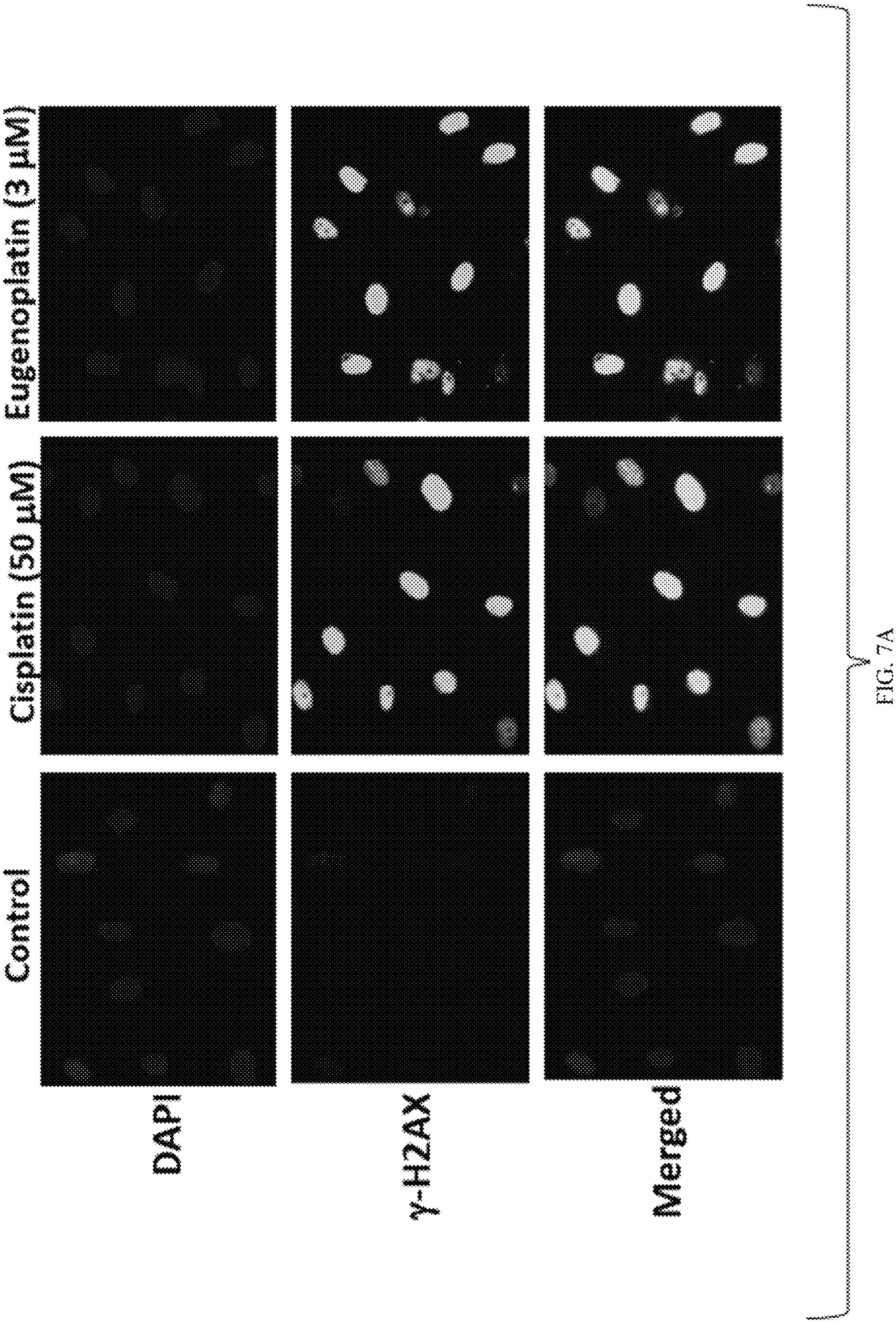
Figure 7B:
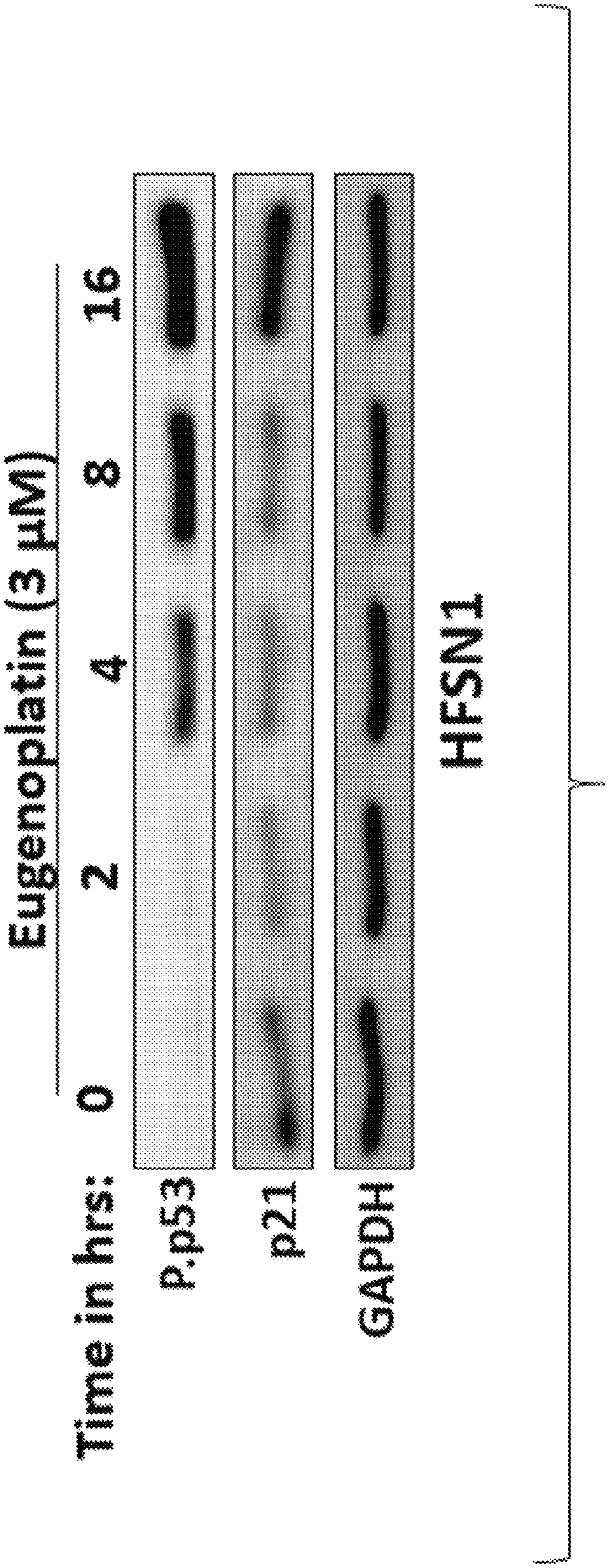

FIGS. 7A-7B. Eugenoplatin triggers DNA damage in human cells.

(7A) Human fibroblast cells (HFSN1) were either sham-treated (DMSO) or challenged with cisplatin (50 μt) or eugenoplatin (3 μM) for 24 h, and then the level of the DNA damage sensing protein (γ-H2AX) was assessed by immunofluorescence.

(7B) Cells were either sham-treated or challenged with cisplatin or eugenoplatin (3 μM) for the indicated periods of time, and then cell lysates were prepared and used for immunoblotting analysis using antibodies against the indicated proteins.

EXAMPLES

1. Materials and Methods 1.1 Cytotoxicity Assay (WST1)

5,000 cells/well were seeded in 96-well plates with appropriate culture media. After cells treatment, WST-1 reagent (Sigma-Aldrich) was added to each well according to the manufacturer's instructions. These experiments were performed in triplicates and were repeated several times.

1.2 Apoptosis Analysis by Annexin V/Flow Cytometry

Cells were harvested, centrifuged and stained with propidium iodide (PI) or PI and Alexa Flour 488 annexin V (Molecular Probes, Eugene), and then were analysed by flow cytometry.

1.3 Immunofluorescence

HFSN1 cells were fixed in formaldehyde (4%) for 19 minutes and blocked with Goat serum (5%), triton X (0.3%) and 1% sodium azide (5%) for 1 hour. The slides were then stained overnight at 4° C. with γ-H2AX antibody (pSer139) (Novusibio) that diluted in BSA (1%), triton X (0.3%) and 1% sodium azide (5%), and subsequently incubated with alexa flour 594-conjugated goat anti-rabbit IgG and DAPI for 1 hour. Images were acquired using fluorescence microscope (Zeiss).

1.4 3D Spheroid Assay

Cells were seeded in 96 well ultra-low attachment plate at a density of 1000 viable cells/well. Cells were cultured in 171 medium supplemented with 1% ABM, 2% B-27, 20 ng/mL EGF, 500 ng/ml HC, 4% FBS and 5 μg/ml insulin. Cells were incubated for 10 days at 37° C. under 5% $CO_2$ Mammospheres with a diameter of ≥100 μm were counted using OPTIKA light microscope.

The features disclosed in the foregoing description, in the claims and/or in the accompanying drawings may, both separately and in any combination thereof, be material for realizing the invention in diverse forms thereof.

REFERENCES

Ali I, Wani W A, Saleem K, Haque A. Platinum compounds: a hope for future cancer chemotherapy. Anticancer Agents Med Chem. 2013; 13 (2):296-306.

Desoize B, Madoulet C. Particular aspects of platinum compounds used at present in cancer treatment. Crit Rev Oncol Hematol. 2002; 42 (3):317-25.

Garcia-Mayea Y, Mir C, Masson F, Paciucci R, ME L L. Insights into new mechanisms and models of cancer stem cell multidrug resistance. Semin Cancer Biol. 2020; 60:166-80.

Islam S S, Al-Sharif I, Sultan A, Al-Mazrou A, Remmal A, Aboussekhra A. Eugenol potentiates cisplatin anti-cancer activity through inhibition of ALDH-positive breast cancer stem cells and the NF-kappaB signaling pathway. Mol Carcinog. 2018; 57 (3):333-46.

Islam S S, Aboussekhra A. Sequential combination of cisplatin with eugenol targets ovarian cancer stem cells through the Notch-Hesl signalling pathway. J Exp Clin Cancer Res. 2019; 38 (1):382.

Tchounwou P B, Dasari S, Noubissi F K, Ray P, Kumar S. Advances in Our Understanding of the Molecular Mechanisms of Action of Cisplatin in Cancer Therapy. J Exp Pharmacol. 2021; 13:303-28.

Volarevic V, Djokovic B, Jankovic M G, Harrell C R, Fellabaum C, Djonov V, Arsenijevic N. Molecular mechanisms of cisplatin-induced nephrotoxicity: a balance on the knife edge between renoprotection and tumor toxicity. J Biomed Sci. 2019; 26 (1):25.

The invention claimed is:

1. A compound comprising a cis-diamminedichloroplatinum II component (cisplatin component) covalently connected to a 2-methoxy-4-(prop-2-en-1-yl)phenol component (eugenol component).

2. A pharmaceutical composition comprising:

(a) a compound of claim 1; and (b) optionally, a pharmaceutically acceptable excipient(s) or carrier.

* * * * *